June 30, 1964 F. W. ANDERSON Plant Pat. 2,415
PLUM TREE
Filed July 22, 1963
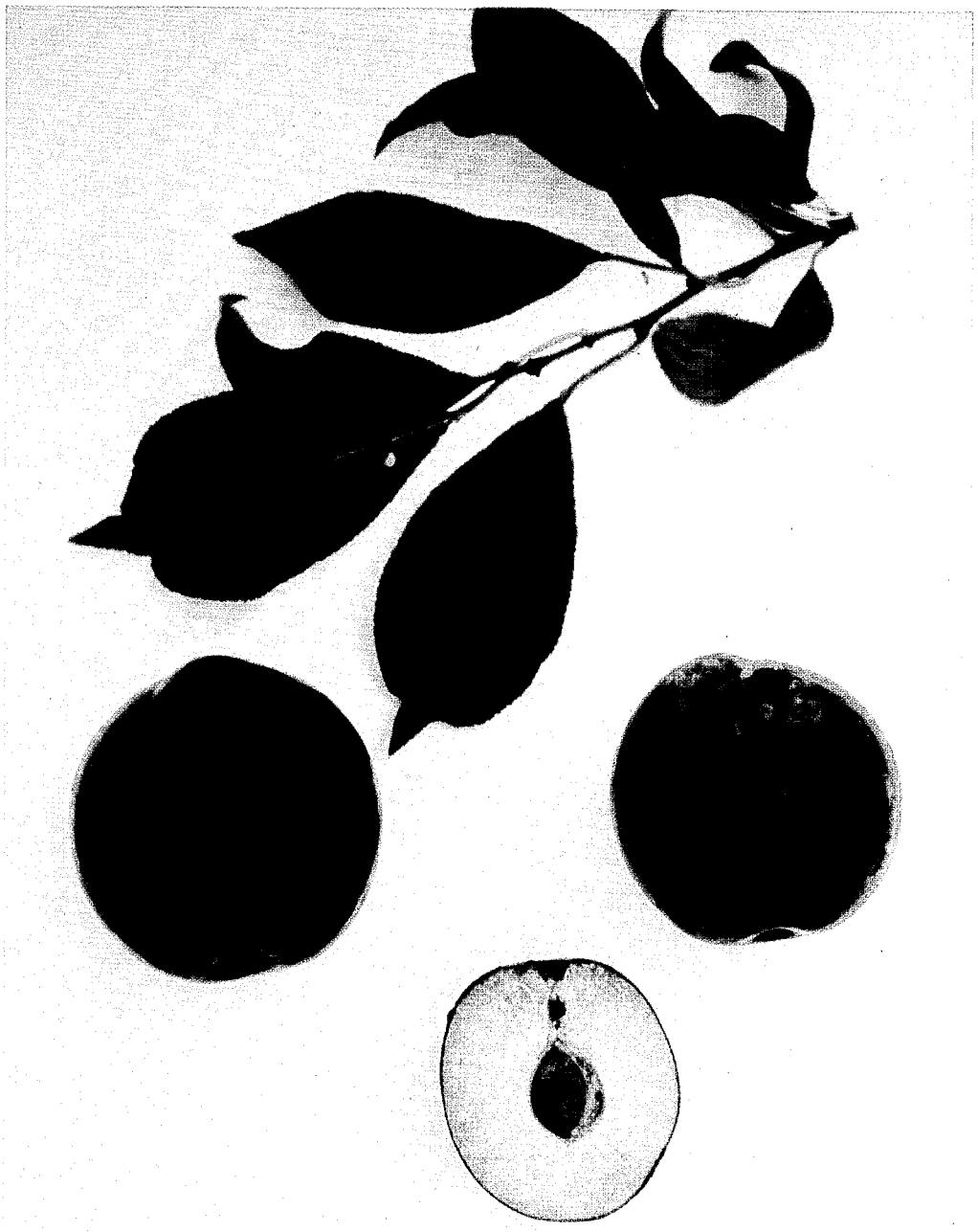
INVENTOR
*Frederic W. Anderson*
*Webster & Webster*
ATTYS.

United States Patent Office

Plant Pat. 2,415
Patented June 30, 1964

2,415
PLUM TREE

Frederic W. Anderson, Merced, Calif., assignor to Kim Bros., doing business as Reedley Nursery, Reedley, Calif., a copartnership Filed July 22, 1963, Ser. No. 296,880
1 Claim. (Cl. Plt.—38)

This invention relates to a new and distinctive variety of plum tree which is a regular and productive bearer of very large, uniform, globose fruit having deep purple-blue skin, yellow flesh, and a free stone.

The present variety of plum tree was originated by me, in my experimental orchard located near Le Grand, Merced County, California, during the course of a long and continuing program seeking improved fruit varieties, including plums.

More particularly, the variety was originated as a seedling of the El Dorado plum (unpatented). A large number of seeds were gathered from open pollenated El Dorado plum trees adjoining a row of Santa Rosa plum (unpatented) trees. The many seedlings, which resulted from planting of such seeds, were maintained by me under careful and continuing observation and when they reached the stage of bearing, one such seedling (which is the instant variety) evidenced the novel and desirable characteristics hereinafter described.

I, therefore, selected the variety for further testing and which included asexual reproduction accomplished by topworking on mature fruit trees in my experimental orchard located as aforesaid. In maturity, all of such asexual reproductions ran true to the parent three in all respects.

In comparison to the El Dorado plum, which it most closely resembles, the present variety bears fruit having quite similar skin color and substantially the same shipping marketing, and eating qualities, but is distinctively characterized by—

(*a*) Large size by a least fifty percent, (*b*) A much more nearly globose shape, and (*c*) A ripening period approximately three to four weeks later.

As the fruit of the present variety is in harvest a considerable time after the El Dorado plum, the marketing period of this type of fruit is thus extended, and which is of substantial commercial benefit.

The drawing comprises an illustration, by photographic reproduction in color, of the fruit and leaves; one fruit being shown as a cut half to expose the flesh, and with the stone remaining in place.

Referring now more specifically to the pomological details of this new and distinct variety of plum tree, the following is an outline description thereof; all major color plate identifications being by reference to Maerz and Paul Dictionary of Color.

Tree:
- *Size.*—Large.
- *Vigor.*—Vigorous.
- *Growth.*—Spreading.
- *Density.*—Open.
- *Production.*—Productive.
- *Bearing.*—Regular bearer.

Trunk:
- *Form.*—Medium.
- *Texture.*—Medium.

Branches:
- *Form.*—Medium.
- *Texture.*—Smooth.

Leaves:
- *Size.*—Average length—4". Average width—1¾".
- *Form.*—Oval; acutely pointed.
- *Thickness.*—Medium.
- *Color.*—Medium green (23–H–7).
- *Texture.*—Smooth.
- *Margin.*—Glandular; crenate.
- *Petiole.*—Medium length; medium thickness.
- *Glands.*—Average number—2 to 4. Alternate; medium size; positioned on petiole and base of blade.

Flower buds:
- *Size.*—Medium.
- *Length.*—Medium.
- *Form.*—Conic.

Flowers: Blooming period— about with Santa Rosa plum; medium as compared with other varieties.

Fruit:
- *Maturity when described.*—Eating ripe—September 1, 1962.
- *Dates of first and last picking.*—August 20, 1962, and September 5, 1962, respectively.
- *Size.*—Uniform; very large. Average diameter axially—2½". Average transversely in suture plane—2½".
- *Form.*—Uniform; symmetrical; globose.
- *Suture.*—Shallow.
- *Ventral surface.*—Rounded.
- *Cavity.*—Average depth—⅝". Average breadth—11/16".
- *Base.*—Rounded.
- *Apex.*—Short; depressed.

Skin:
- *Thickness.*—Thick.
- *Texture.*—Tough.
- *Tendency to crack.*—None.
- *Color.*—Deep purple-blue (48–C–11).

Flesh:
- *Color.*—Medium yellow (11–F–5).
- *Texture.*—Medium; meaty.
- *Fibers.*—Tender.
- *Ripens.*—Evenly.
- *Flavor.*—Vinous.
- Eating quality.—Good to excellent.

Stone:
- *Type.*—Free.
- *Size.* — Small. Average length — ⅞". Average breadth—⅝". Average thickness—5/16".
- *Form.*—Oval.
- *Base.*—Straight.
- *Apex.*—Rounded.
- *Sides.*—Equal.
- *Color.*—Reddish brown (7–L–7).
- *Tendency to split.*—None.

Use: Local; dessert; long distance shipping.
Keeping quality: Good.
Shipping quality: Good.

The plum tree and its fruit herein described may vary in slight detail due to climatic and soil conditions under which the variety may be grown; the present description being of the variety as grown in the Central Valley of California.

The following is claimed:

A new and distinct variety of plum tree, substantially as illustrated and described, which is a regular and productive bearer of very large, uniform, globose fruit having deep purple-blue skin, yellow flesh, and a free stone; the variety being further distinctively characterized, as to novelty, and in comparsion to the El Dorado plum, by fruit which is at least fifty percent larger in size, much more nearly globose in shape, and in harvest approximately three to four weeks later.

No references cited.